US007909800B2

(12) United States Patent
Cazzini

(10) Patent No.: US 7,909,800 B2
(45) Date of Patent: Mar. 22, 2011

(54) JUXTASCLERAL DRUG DELIVERY AND OCULAR IMPLANT SYSTEM

(75) Inventor: Karl Cazzini, Lindenhurst, IL (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 12/685,099

(22) Filed: Jan. 11, 2010

(65) Prior Publication Data

US 2010/0114039 A1     May 6, 2010

Related U.S. Application Data

(62) Division of application No. 12/121,062, filed on May 15, 2008, now abandoned.

(60) Provisional application No. 60/953,054, filed on Jul. 31, 2007.

(51) Int. Cl.
*A61M 5/24* (2006.01)

(52) U.S. Cl. .......................... 604/200; 604/181; 604/244

(58) Field of Classification Search .......... 604/520–521, 604/57, 59–64, 82, 84, 87–88, 244, 93.01, 604/131, 151–152, 181, 184–185, 187, 200–203, 604/218
See application file for complete search history.

(56) References Cited

U.S. PATENT DOCUMENTS

| 2,022,065 | A |   | 11/1935 | Wappler |
| 2,591,457 | A |   | 4/1952 | Maynes |
| 4,900,303 | A | * | 2/1990 | Lemelson ............... 604/514 |
| 4,968,296 | A |   | 11/1990 | Ritch et al. |
| 4,990,135 | A |   | 2/1991 | Truesdale, Jr. |
| 5,167,641 | A |   | 12/1992 | Schmitz |
| 5,242,449 | A |   | 9/1993 | Zaleski |
| 5,702,414 | A |   | 12/1997 | Richter et al. |
| 6,283,949 | B1 |   | 9/2001 | Roorda |
| 6,397,849 | B1 |   | 6/2002 | Bowman et al. |
| 6,899,717 | B2 |   | 5/2005 | Weber et al. |
| 2005/0143363 | A1 |   | 6/2005 | De Juan et al. |
| 2009/0012595 | A1 |   | 1/2009 | Seliktar et al. |

FOREIGN PATENT DOCUMENTS

| WO | 02089767 A1 | 11/2002 |
| WO | 03000312 A2 | 1/2003 |

OTHER PUBLICATIONS

Guttman, "Cannula approach using posterior delivery brings unparalleled safety"; Ophthalmology Times, Mar. 1, 2003, 2 pgs.
Peterson, L., "Age-Related Macular Degeneration"; Trends-in-Medicine, May 2002, 6 pgs.

* cited by examiner

*Primary Examiner* — Theodore J Stigell
(74) *Attorney, Agent, or Firm* — W. David Lee

(57) ABSTRACT

Ophthalmic drug delivery devices useful for delivery of pharmaceutically active agents to the posterior segment of the eye are disclosed.

8 Claims, 4 Drawing Sheets

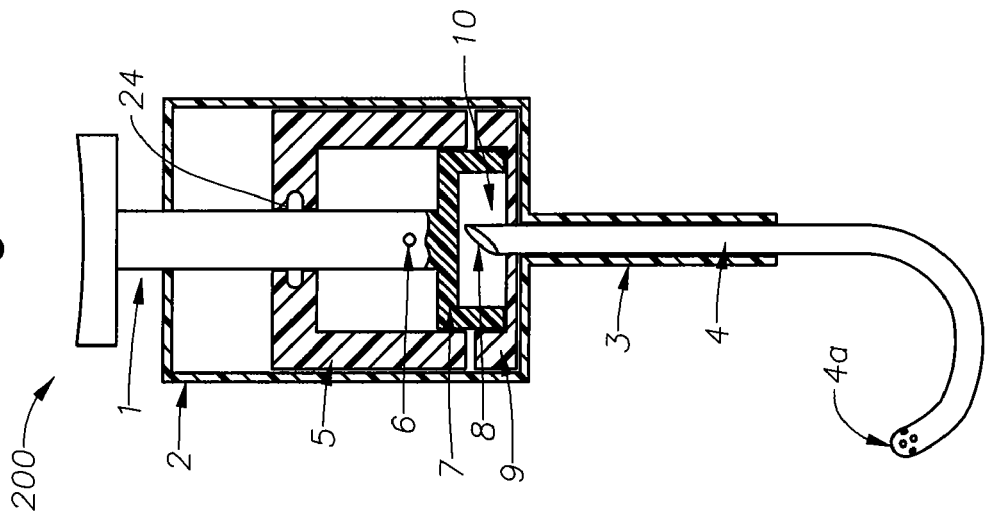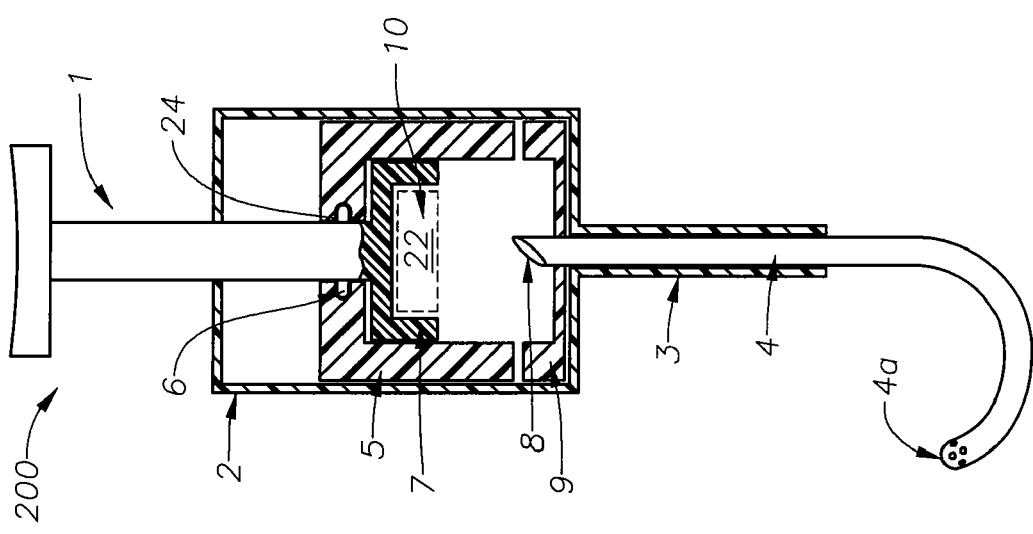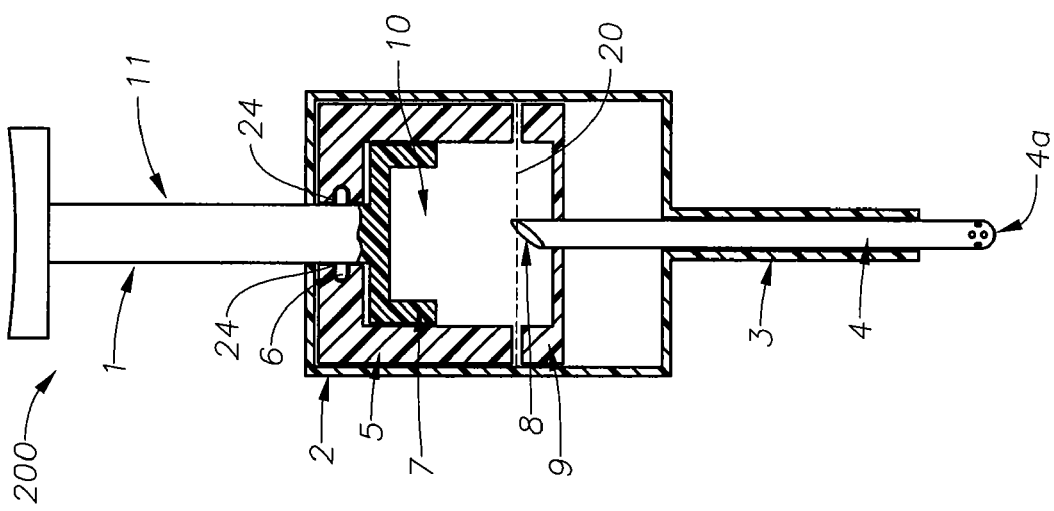

JUXTASCLERAL DRUG DELIVERY AND OCULAR IMPLANT SYSTEM

This application is a divisional of U.S. application Ser. No. 12/121,062 filed May 15, 2008, now abandoned, which claims priority to U.S. Provisional Patent Application 60/953,054 filed Jul. 31, 2007.

FIELD OF THE INVENTION

The present invention generally pertains to instruments for localized delivery of pharmaceutically active agents to body tissue. More particularly, but not by way of limitation, the present invention pertains to instruments for localized delivery of pharmaceutically active agents to the posterior segment of the eye.

DESCRIPTION OF THE RELATED ART

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

Age related macular degeneration (ARMD) is the leading cause of blindness in the elderly. ARMD attacks the center of vision and blurs it, making reading, driving, and other detailed tasks difficult or impossible. About 200,000 new cases of ARMD occur each year in the United States alone. Current estimates reveal that approximately forty percent of the population over age 75, and approximately twenty percent of the population over age 60, suffer from some degree of macular degeneration. "Wet" ARMD is the type of ARMD that most often causes blindness. In wet ARMD, newly formed choroidal blood vessels (choroidal neovascularization (CNV)) leak fluid and cause progressive damage to the retina.

In the particular case of CNV in ARMD, three main methods of treatment are currently being developed, (a) photocoagulation, (b) the use of angiogenesis inhibitors, and (c) photodynamic therapy. Photocoagulation is the most common treatment modality for CNV. However, photocoagulation can be harmful to the retina and is impractical when the CNV is near the fovea. Furthermore, over time, photocoagulation often results in recurrent CNV. Oral or parenteral (non-ocular) administration of anti-angiogenic compounds is also being tested as a systemic treatment for ARMD. However, due to drug-specific metabolic restrictions, systemic administration usually provides sub-therapeutic drug levels to the eye. Therefore, to achieve effective intraocular drug concentrations, either an unacceptably high dose or repetitive conventional doses are required. Periocular injections of these compounds often result in the drug being quickly washed out and depleted from the eye, via periocular vasculature and soft tissue, into the general circulation. Repetitive intraocular injections may result in severe, often blinding, complications such as retinal detachment and endophthalmitis. Photodynamic therapy is a new technology for which the long-term efficacy is still largely unknown.

In order to prevent complications related to the above-described treatments and to provide better ocular treatment, researchers have suggested various implants aimed at localizing delivery of anti-angiogenic compounds to the eye. U.S. Pat. No. 5,824,072 to Wong discloses a non-biodegradable polymeric implant with a pharmaceutically active agent disposed therein. The pharmaceutically active agent diffuses through the polymer body of the implant into the target tissue. The pharmaceutically active agent may include drugs for the treatment of macular degeneration and diabetic retinopathy. The implant is placed substantially within the tear fluid upon the outer surface of the eye over an avascular region, and may be anchored in the conjunctiva or sclera; episclerally or intrasclerally over an avascular region; substantially within the suprachoroidial space over an avascular region such as the pars plana or a surgically induced avascular region; or in direct communication with the vitreous.

U.S. Pat. No. 5,476,511 to Gwon et al. discloses a polymer implant for placement under the conjunctiva of the eye. The implant may be used to deliver neovascular inhibitors for the treatment of ARMD and drugs for the treatment of retinopathies, and retinitis. The pharmaceutically active agent diffuses through the polymer body of the implant.

U.S. Pat. No. 5,773,019 to Ashton et al. discloses a non-bioerodible polymer implant for delivery of certain drugs including angiostatic steroids and drugs such as cyclosporine for the treatment of uveitis. Once again, the pharmaceutically active agent diffuses through the polymer body of the implant.

All of the above-described implants require careful design and manufacture to permit controlled diffusion of the pharmaceutically active agent through a polymer body (i.e., matrix devices) or polymer membrane (i.e., reservoir devices) to the desired site of therapy. Drug release from these devices depends on the porosity and diffusion characteristics of the matrix or membrane, respectively. These parameters must be tailored for each drug moiety to be used with these devices. Consequently, these requirements generally increase the complexity and cost of such implants.

U.S. Pat. No. 5,824,073 to Peyman discloses an indentor for positioning in the eye. The indentor has a raised portion that is used to indent or apply pressure to the sclera over the macular area of the eye. This patent discloses that such pressure decreases choroidal congestion and blood flow through the subretinal neovascular membrane, which, in turn, decreases bleeding and subretinal fluid accumulation.

Therefore, a need exists for an ophthalmic drug delivery device for the creation of a posterior juxtascleral depot containing a pharmaceutically active agent. The device should be capable of safe, effective, rate-controlled, localized delivery of a wide variety of pharmaceutically active agents. The procedure for using such a device should be safe, simple, quick, and capable of being performed in an outpatient setting. Ideally, such a device should be easy and economical to manufacture. Such a device is especially needed for localized delivery of pharmaceutically active agents to the posterior segment of the eye to combat ARMD, CNV, retinopathies, retinitis, uveitis, macular edema, glaucoma, and neuropathies.

SUMMARY OF THE INVENTION

In one aspect, the present invention is an ophthalmic drug delivery device having an injector housing, a capsule containing a pharmaceutically active agent disposed within the injector housing, a delivery cannula coupled to a distal surface of the injector housing, an injector cannula slidably disposed within the delivery cannula and the injector housing, an extension assembly for extending the injector cannula from the delivery cannula, and a compression assembly. The injector cannula has a first tip for penetrating the capsule, and a second tip for dispensing the pharmaceutically active agent. The compression assembly compresses the capsule and allows delivery of the pharmaceutically active agent.

In another aspect, the present invention is an ophthalmic drug delivery device having an injector housing; a delivery cannula coupled to a distal surface of said injector housing; an injector cannula slidably disposed within said delivery cannula and said injector housing, said injector cannula having a first opening proximate a distal tip; a mandrel slidably disposed within said injector cannula; an extension assembly for extending said injector cannula from said delivery cannula; and a drug eluting implant disposed within said injector cannula.

BRIEF DESCRIPTION OF THE DRAWINGS

For a more complete understanding of the present invention, and for further objects and advantages thereof, reference is made to the following description taken in conjunction with the accompanying drawings in which:

FIG. 3 is a schematic view of the drug delivery device of the present invention showing the injector cannula in the fully retracted position;

FIG. 4 is a schematic view of the device of FIG. 3 showing the injector cannula in the fully deployed position;

FIG. 5 is a schematic view of the device of FIG. 3 showing the plunger shaft unlocked from the positioning member;

DETAILED DESCRIPTION OF THE PREFERRED EMBODIMENTS

The preferred embodiments of the present invention and their advantages are best understood by referring to FIGS. 1-10 of the drawings, like numerals being used for like and corresponding parts of the various drawings.

Figure 1:
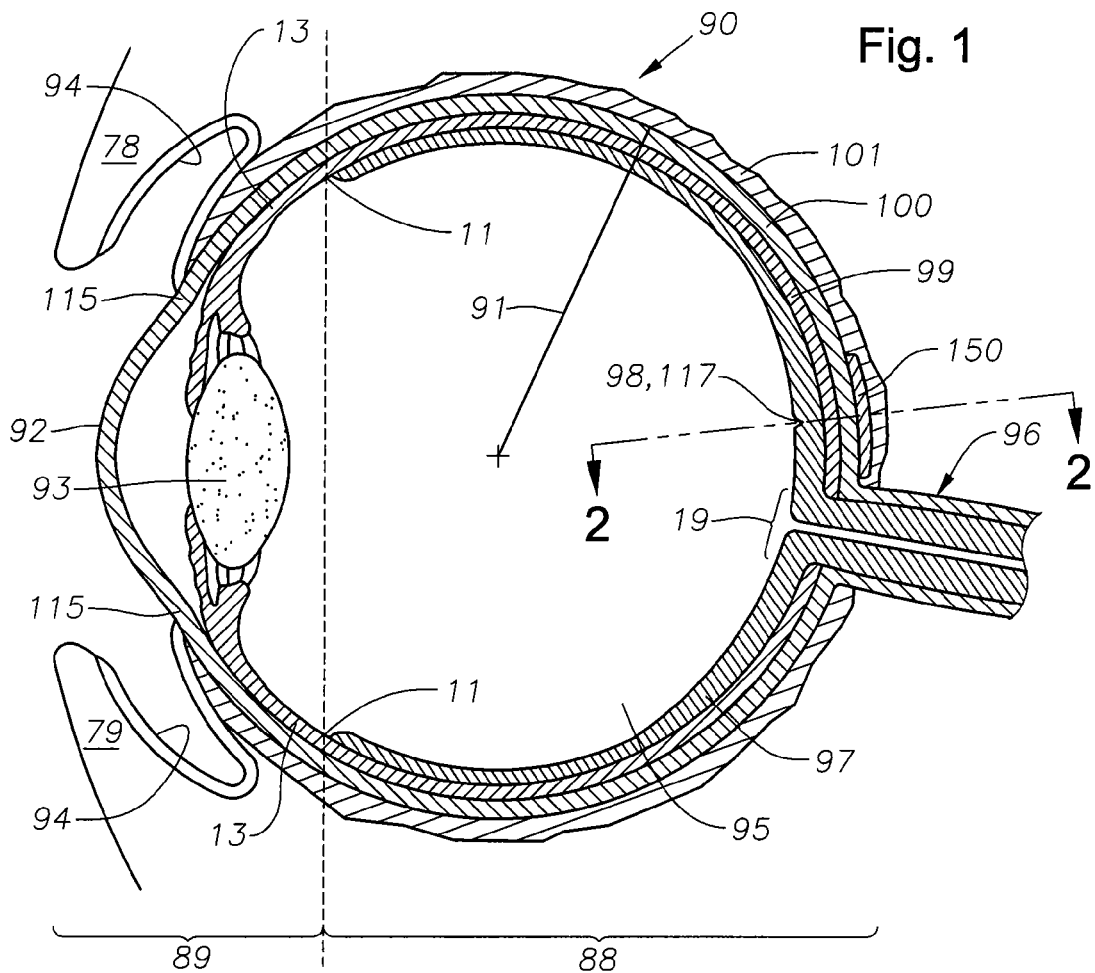
FIG. 1 is a side sectional view schematically illustrating the human eye and a posterior juxtascleral depot in the posterior segment of the eye according to the present invention.
Figure 2:
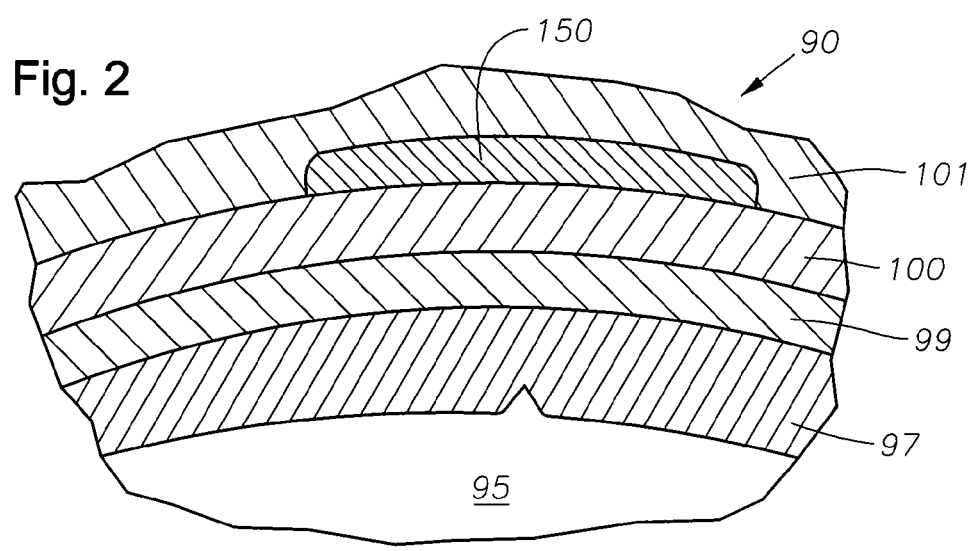
FIG. 2 is detailed cross-sectional view of the eye of FIG. 1 along line 2-2.

FIGS. 1-2 illustrate various portions of the human eye important to a complete understanding of the present invention. Referring first to FIG. 1, a human eye 90 is schematically illustrated. Eye 90 has a cornea 92, a lens 93, vitreous 95, a sclera 100, a choroid 99, a retina 97, and an optic nerve 96. Eye 90 is generally divided into an anterior segment 89 and a posterior segment 88. Anterior segment 89 of eye 90 generally includes the portions of eye 90 anterior of ora serata 11. Posterior segment 88 of eye 90 generally includes the portions of eye 90 posterior of ora serata 11. Retina 97 is physically attached to choroid 99 in a circumferential manner proximate pars plana 13. Retina 97 has a macula 98 located slightly lateral to optic disk 19. As is well known in the ophthalmic art, macula 98 is comprised primarily of retinal cones and is the region of maximum visual acuity in retina 97. At the center of macula 98 is a fovea 117. A Tenon's capsule or Tenon's membrane 101 is disposed on sclera 100. A conjunctiva 94 covers a short area of the globe of eye 90 posterior to limbus 115 (the bulbar conjunctiva) and folds up (the upper cul-de-sac) or down (the lower cul-de-sac) to cover the inner areas of upper eyelid 78 and lower eyelid 79, respectively. The bulbar conjunctiva 94 is disposed on top of Tenon's capsule 101.

As is shown in FIGS. 1 and 2, and as is described in greater detail hereinbelow, a posterior juxtascleral drug depot 150 containing a pharmaceutically active agent is preferably disposed directly on the outer surface of sclera 100, below Tenon's capsule 101 for treatment of posterior segment ophthalmic diseases or conditions. Depot 150 may be used in humans or animals.

FIG. 3 illustrates the preferred embodiment of a device 200 for the creation of posterior juxtascleral depot 150. An injector housing 2 encloses a positioning member 5 surrounding a compression member 7. Injector cannula guide 9 is affixed to an injector cannula 4, which is free to slide inside a delivery cannula 3. As shown in FIG. 4, a sealed polymer capsule 22 containing a predetermined dose of a fluidized pharmaceutical preparation is loaded into capsule space 10, by opening injector housing 2 along line 20. Alternatively, capsule 22 could be prepackaged inside a sealed injector housing 2 within the capsule space 10. The surgeon makes a small incision in conjunctiva 94, presents delivery cannula 3 to the conjunctival incision, and advances injector cannula 4 into the space between Tenons capsule 101 and sclera 100, by slowly depressing plunger shaft 1, as shown in FIG. 4. Plunger shaft 1 is locked and engaged with slots 24 located in the positioning member 5, by means of a locking member 6, such as to prevent drug capsule 22 from being ruptured during advancement of injector cannula 4. Visible reference markings 11 may be placed on the outside of the plunger shaft 1, thereby alerting the surgeon as to the precise position of injector tip 4a. Alternatively, a light guide (not shown) may be used to deliver light to the blunt injector tip 4a, enabling the position of tip 4a to be determined by trans-scleral illumination. Once injector cannula 4 is in the desired drug delivery position, the surgeon rotates plunger shaft 1 ninety degrees to disengage locking member 6 from slots 24 within positioning member 5. As shown in FIG. 5, further depression of plunger shaft 1 allows compression member 7 to impale drug capsule 22 on penetrating tip 8 of injector cannula 4. Still further depression of plunger shaft 1 allows compression member 7 to compress capsule 22, thereby forcing the fluidized drug to flow through injector cannula 4, and exit injector tip 4a at the desired injection site.

Injector cannula 4 is preferably made from a superelastic Nitinol tube, which has been preformed by means well known to those skilled in the art, to retain and follow the profile of the outer globe of sclera 100 during advancement to and retreat from the posterior juxtascleral injection site. This mechanism guarantees a safe and efficacious means for delivering a posterior juxtascleral depot to posterior segment 88.

Figure 6:
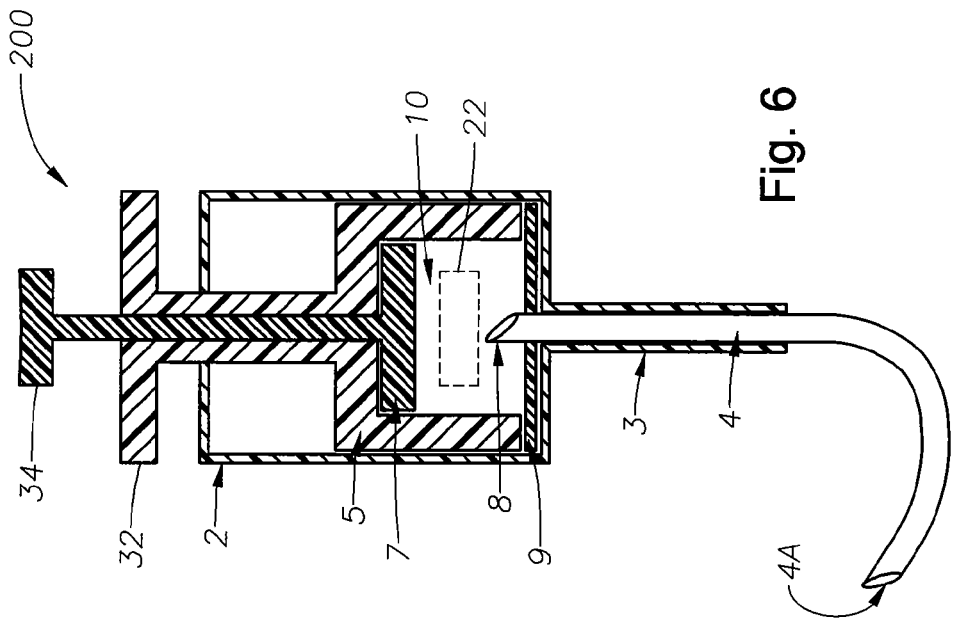
FIG. 6 is a schematic view of an alternative embodiment of the drug delivery device of the present invention.

FIG. 6 illustrates an alternative embodiment of device 200. In this embodiment, depression of plunger 32 extends injector cannula 4 to the desired location for making the drug depot. The drug is delivered by depressing plunger 34, which punctures drug containing capsule 22, and directs it to the injection site. In a refinement of this embodiment, a protective sheath (not shown) may be placed over injector cannula 4 to protect surrounding tissues during deployment of the injector cannula 4. This sheath could be illuminated to provide a trans-scleral illumination of the distal tip 4a of injector cannula 4.

Figure 7:
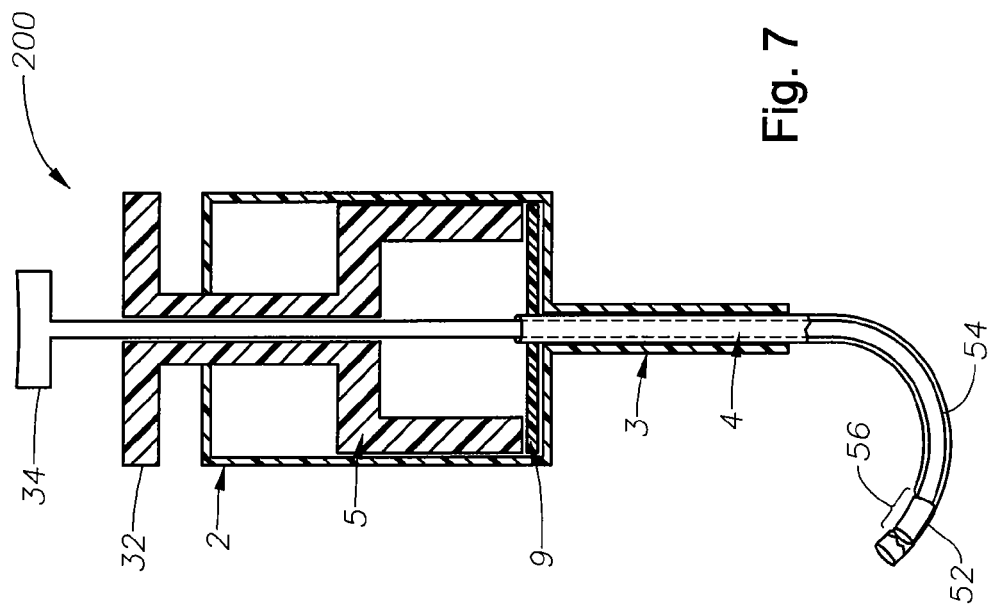
FIG. 7 is a schematic view of a second alternative embodiment of the drug delivery device of the present invention.
Figure 8:
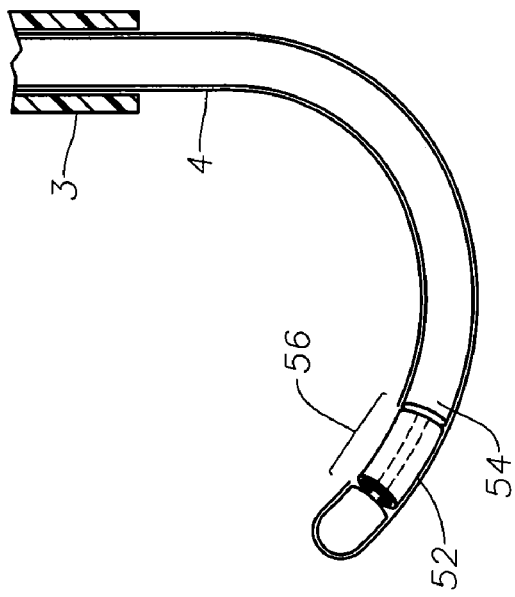
FIGS. 8-10 are enlarged, fragmentary, schematic views of an alternate embodiment of the implant of the device of FIG. 7.
Figure 9:
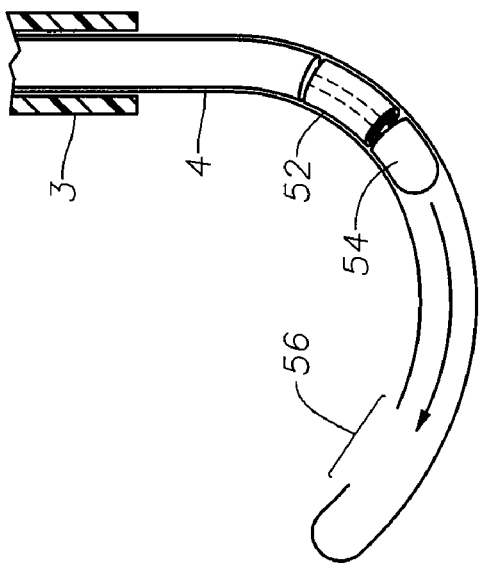
Figure 10:
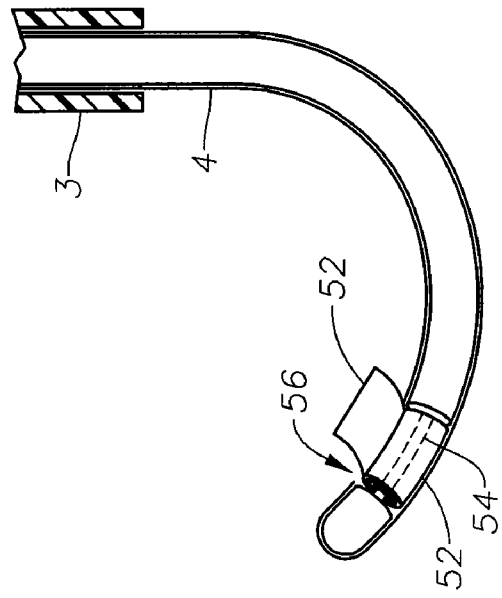

FIG. 7 illustrates a further embodiment of device 200 in which the device has been modified to deliver a drug eluting polymer implant 52. Such a drug-eluting implant could be fabricated from a biocompatible and bio-erodible carrier matrix such as poly-DL-lactide-co-glycolide (PLG). Other suitable carrier materials are well known to those skilled in the art. FIGS. 8-10 depict an alternate embodiment of this concept, illustrating how a biodegradable/bio-erodible ocular strip implant 52 is deployed using the methods described for a juxtascleral injection. In this case, strip 52 encapsulates the pharmaceutical preparation prescribed. Drug-eluting strip 52 is wound onto flexible delivery mandrel 54 and guided to the end of injector cannula 4. Once in position, drug eluting strip 52 may be unfurled by a mechanism which rotates delivery mandrel 54, causing strip 52 to unroll and exit through delivery aperture 56. In so doing, drug-eluting strip 52 may be deployed flat, within the confines of the sub-Tenons space, and assume its drug delivery function.

From the above, it may be appreciated that the present invention provides improved devices and methods for safe, effective, rate-controlled, localized delivery of a variety of pharmaceutically active agents to the eye, and particularly to the posterior segment of the eye to combat ARMD, CNV, retinopathies, retinitis, uveitis, macular edema, glaucoma, and neuropathies.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An ophthalmic drug delivery device, comprising:
   an injector housing;
   a polymer capsule containing a fluidized pharmaceutically active agent, said capsule disposed within said injector housing;
   a delivery cannula coupled to a distal surface of said injector housing;
   an injector cannula slidably disposed within said delivery cannula and said injector housing, said injector cannula having a penetrating tip for impaling said capsule, and a second tip for dispensing said pharmaceutically active agent, wherein the polymer capsule is initially spaced away from the injector cannula;
   an extension assembly for extending said injector cannula from said delivery cannula; and
   a compression assembly for compressing said capsule over the penetrating tip to deliver said pharmaceutically active agent.

2. The drug delivery device of claim 1 wherein said extension assembly comprises:
   a first plunger shaft slidably disposed in said injector housing;
   a positioning member coupled to said first plunger shaft and disposed within said injector housing; and
   an injector cannula guide coupled to said injector cannula and disposed within said injector housing beneath said positioning member;
   whereby depression of said first plunger shaft displaces said positioning member and said injector cannula guide to extend said injector cannula from said delivery cannula.

3. The drug delivery device of claim 2 wherein said compression assembly comprises:
   a compression member coupled to said first plunger shaft; and
   a locking mechanism for removably coupling said first plunger shaft and said positioning member.

4. The drug delivery device of claim 2 wherein said compression assembly comprises:
   a second plunger shaft slidably disposed within said first plunger shaft; and
   a compression member coupled to said second plunger shaft.

5. The drug delivery device of claim 1 wherein said injector cannula is made from a superelastic material.

6. The drug delivery device of claim 1 wherein said injector housing may be opened so as to enable placement of said capsule.

7. The drug delivery device of claim 1 wherein said capsule is disposed within said injector housing, and said injector housing is sealed.

8. An ophthalmic drug delivery device, comprising:
   an injector housing;
   a capsule containing a pharmaceutically active agent, said capsule disposed within said injector housing;
   a delivery cannula coupled to a distal surface of said injector housing;
   an injector cannula slidably disposed within said delivery cannula and said injector housing, said injector cannula having a first tip for penetrating said capsule, and a second tip for dispensing said pharmaceutically active agent;
   an extension assembly for extending said injector cannula from said delivery cannula, wherein said extension assembly comprises:
     a first plunger shaft slidably disposed in said injector housing;
     a positioning member coupled to said first plunger shaft and disposed within said injector housing; and
     an injector cannula guide coupled to said injector cannula and disposed within said injector housing beneath said positioning member;
     whereby depression of said first plunger shaft displaces said positioning member and said injector cannula guide to extend said injector cannula from said delivery cannula; and
   a compression assembly for compressing said capsule and allowing delivery of said pharmaceutically active agent, wherein said compression assembly comprises:
     a second plunger shaft slidably disposed within said first plunger shaft; and
     a compression member coupled to said second plunger shaft.

* * * * *